United States Patent
Jolly (10) Patent No.: US 10,981,810 B2
(45) Date of Patent: Apr. 20, 2021

(54) ELECTRO-ANALYTICAL SYSTEM FOR MONITORING TOTAL ORGANIC CARBON IN A WATER SOURCE

(71) Applicant: Environmental and Life Support Technology, LLC, Parker, CO (US)

(72) Inventor: Clifford D. Jolly, Parker, CO (US)

(*) Notice: Subject to any disclaimer, the term of this patent is extended or adjusted under 35 U.S.C. 154(b) by 50 days.

(21) Appl. No.: 16/416,917

(22) Filed: May 20, 2019

(65) Prior Publication Data

US 2019/0352200 A1 Nov. 21, 2019

Related U.S. Application Data (60) Provisional application No. 62/673,611, filed on May 18, 2018.

(51) Int. Cl.
| | | |
|---|---|---|
| C02F 1/467 | (2006.01) | |
| C02F 1/72 | (2006.01) | |
| C02F 1/461 | (2006.01) | |
| C02F 9/00 | (2006.01) | |
| C02F 101/30 | (2006.01) | |

(52) U.S. Cl.
CPC ........ *C02F 1/4672* (2013.01); *C02F 1/46109* (2013.01); *C02F 1/72* (2013.01); *C02F 9/005* (2013.01); *C02F 2101/30* (2013.01); *C02F 2201/46125* (2013.01)

(58) Field of Classification Search
None
See application file for complete search history.

(56) References Cited

U.S. PATENT DOCUMENTS

| | | | |
|---|---|---|---|
| 4,523,584 A | | 6/1985 | Yachia et al. |
| 4,828,718 A | * | 5/1989 | Habermann ......... B01J 31/1616 210/763 |
| 5,176,836 A | | 1/1993 | Sauer et al. |
| 5,186,842 A | | 2/1993 | Jolly |
| 5,244,478 A | | 9/1993 | Jolly |
| 5,312,756 A | | 5/1994 | Jolly |
| 5,427,667 A | | 6/1995 | Bakhir et al. |

(Continued)

OTHER PUBLICATIONS

Int'l Search Report & Written Opinion (PCT/US2019/042782), dated Oct. 3, 2019.

(Continued)

*Primary Examiner* — J. Christopher Ball
(74) *Attorney, Agent, or Firm* — Gregory L. Porter; Hunton Andrews Kurth LLP (57) ABSTRACT

An automated total organic carbon analyzer is described. Embodiments of the system include two features, namely the development of a selective oxidation reactor to oxidize organic contaminants to their corresponding organic acids, and the measurement of the organic acids individually by chain length using an electroanalytical detector. Combining this electroanalytical approach with sequential detection capabilities (such as spectrophotometry) can expand the instrument capabilities by providing organic contaminant speciation. The described reactor performs selective oxidation of organic carbon to organic acids followed by complexation with a proprietary ligand, then selective detection using electroanalytical accumulation and desorption of organic acids performed at an electrode surface.

9 Claims, 6 Drawing Sheets

(56) References Cited

U.S. PATENT DOCUMENTS

| | | |
|---|---|---|
| 5,445,594 A | 8/1995 | Elist |
| 5,559,035 A | 9/1996 | Jolly |
| 5,899,849 A | 5/1999 | Elist |
| 8,986,193 B1 | 3/2015 | Elist |
| 9,877,835 B1 | 1/2018 | Loria |
| 2005/0173242 A1 | 8/2005 | Elgressy |
| 2014/0031619 A1 | 1/2014 | Moon |
| 2016/0340206 A1 | 11/2016 | Antos |
| 2017/0020700 A1 | 1/2017 | Bienvenu et al. |
| 2018/0297869 A1 | 10/2018 | Martikainen et al. |

OTHER PUBLICATIONS

Int'l Search Report & Written OPinion (PCT/US2019/036590), dated Oct. 4, 2019.

* cited by examiner

Figure 1. Schematic of TOC System (100)

Test Conditions: 20 ug/l acetic acid + 1.0 mg/l Ligand in de-ionized water, pH 6.2

Figure 8. Comparison of Organic Acid Complex Peaks by Varying Scan Methods

ELECTRO-ANALYTICAL SYSTEM FOR MONITORING TOTAL ORGANIC CARBON IN A WATER SOURCE

CROSS-REFERENCE TO RELATED APPLICATIONS

This application claims priority from U.S. Provisional Application No. 62/673,611, filed on May 18, 2019, the disclosure of which is incorporated herein by reference in its entirety.

FIELD OF INVENTION

The present inventions are related to monitoring organic carbon contamination in a water sources. The systems and methods disclosed incorporate oxidation reactors and electroanalytical detection platforms. More specifically, the present inventions relate to the partial oxidation of organic contaminants to their corresponding organic acids without deep oxidation to carbon dioxide or other inorganic carbon compounds.

BACKGROUND AND SUMMARY

Traditional processes for measuring and/or monitoring the Total Organic Carbon (TOC) within a solution seek to fully oxidize organic compounds in water to $CO_2$ (deep oxidation) and then measures the $CO_2$ by conductivity, non-dispersive infrared analysis (NDIR), or other known techniques. This method suffers from the complexity of engineering detection methods for $CO_2$, and significant interference from contaminates, such as, inorganic carbon present as dissolved $CO_2$, bicarbonates and carbonates in the process water. Existing methods require that $CO_2$ be purged from the sample, which removes volatile organic components along with the $CO_2$, yielding a measurement that is often less than true TOC.

Disclosed is a system and technique for selective catalytic oxidization of organic contaminants to their corresponding organic acids. Typically, oxidation of an organic contaminant to an organic acid is a fast process, whereas the oxidation of the organic acid to CO2 is a slower and rate-limiting step. This is due at least in part to resonance stabilization of the carbonyl groups on the acids. By operating at lower temperatures and with highly selective catalysts, the disclosed system and methods can ensure that a quantitative amount of organic acid is produced and that $CO_2$ formation is minimal. Since $CO_2$ does not interfere with the measurement of the organic acids to at least three orders of magnitude in concentration excess, there is no need to remove it from the process water, vastly simplifying the TOC measurement process.

Using this approach, wide ranges of contaminants can be converted to organic acids, then the organic acids can be analyzed electroanalytically and differentiated by carbon chain length. Their sum total will give true Total Organic Carbon (TOC), not just "Non-Purgeable Organic Carbon" as is obtained from current UV-persulfate and related methods that do not measure volatiles lost during removal of total inorganic carbon (TIC) from the sample or process water. The resultant organic acid data, combined with data that can be obtained from the spectrophotometric analysis, will yield a simple method to determine true total organic carbon quantitation and classification.

In certain disclosed embodiments, feedback from a catalytic reactor to an embedded controller allows smart oxidation to be managed so that the reaction conditions can be adapted to the organic contaminant load in each sample and/or adapted as process contamination levels and species change. This methodology can be used to ensure deep oxidation is minimized or avoided.

The disclosed systems, methods, and techniques provide significant benefits including, for example, in some embodiments, deep oxidation (i.e. oxidation to CO2) is not required, thereby eliminating TIC interference. In some embodiments, no gas/liquid separation is required in process, therefore there are no gas entrainment problems, which may yield higher reliability and simplify operation by elimination of two-phase flow. In some embodiments, expendables requirements are reduced and no hazardous or toxic materials are required. In some embodiments, the disclosed reactor provides a solid oxidant, therefore, oxygen gas or liquid oxidants are not required. In some embodiments, detection limits in the parts-per-trillion (ppt) range are attainable. The sensitivity provided by the electroanalytical detection techniques allows sample volumes to be adjusted automatically to achieve specified detection range. In some embodiments, the electrocatalytic reactor requires only low or reduced power to operate. Some embodiments comprise the potential to provide some speciation capability to help determine the nature of the components making up the TOC contamination. Some embodiments comprise the capability for full automation by using in situ calibration standards and advanced smart embedded control.

The conventional TOC approaches require strong acids, purge gases (or membranes), mechanical pumps, valves and additional mechanical complications to remove TIC from the sample before TOC measurement. In some water sources, high TIC levels are likely; therefore, the TIC must be removed prior to low-level TOC analysis. In the disclosed approach, selective oxidation of organics to organic acids followed by selective detection of the organic acids eliminates the need to remove the TIC. This simplifies the system significantly.

DETAILED DESCRIPTION

The following description of embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

In some embodiments, the disclosed design allows for automated calibration and quality control/quality assurance sample analysis over long operational periods. In some embodiments, this process approach does not require expendable liquid reagents for operation. The disclosed designs may be utilized for unattended analysis of ultra-pure and drinking water streams due to their simplicity and independence of TIC concentrations.

Figure 1:
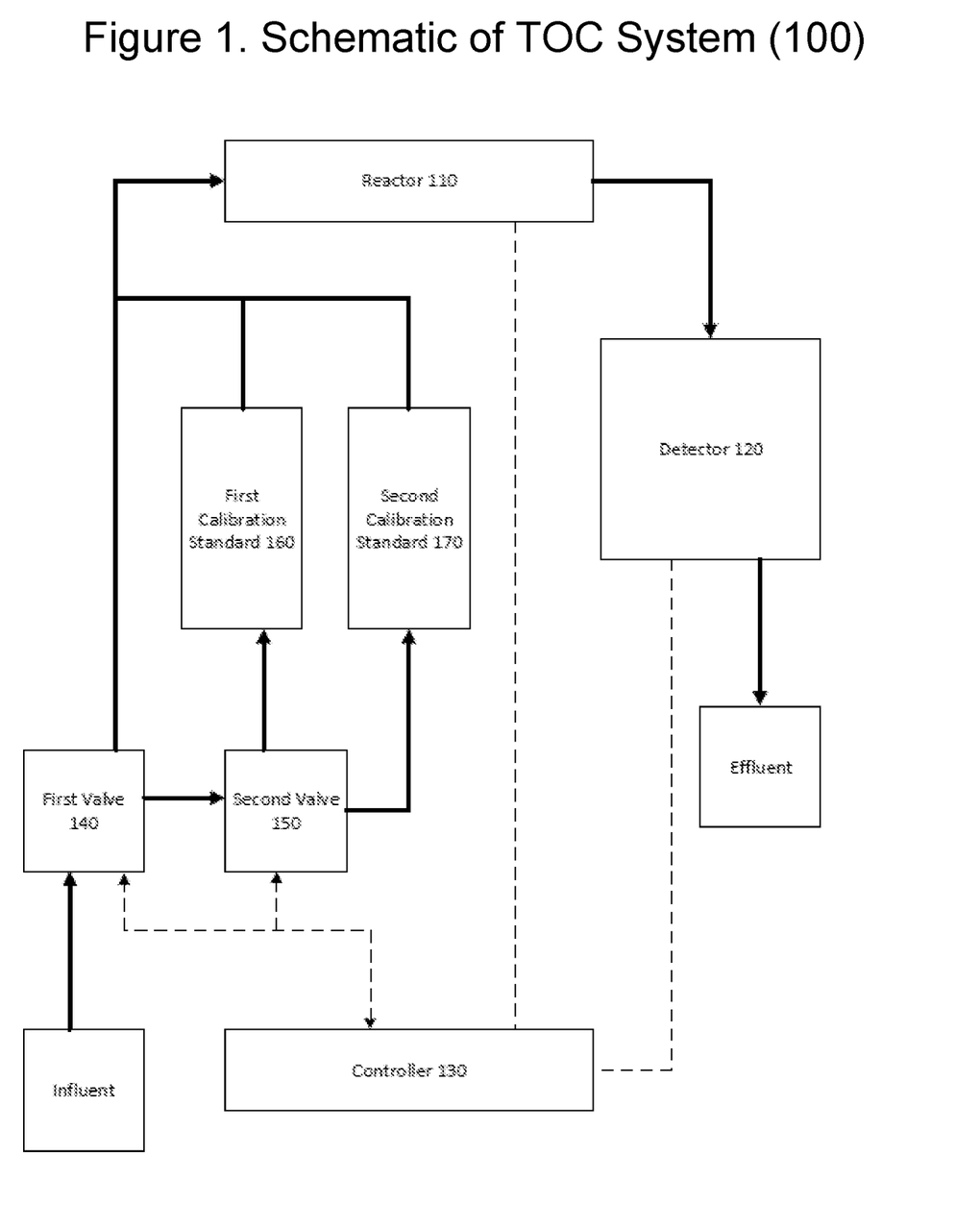
FIG. 1 is a schematic diagram of a total organic carbon system according to an example embodiment.

FIG. 1 shows a schematic of the disclosed TOC system according to an example embodiment. As further discussed below, system 100 may be incorporated into a water stream comprising an influent and effluent. System 100 may comprise a reactor 110, an electroanalytic detector 120, a controller 130, a first valve 140, a second valve 150, a first calibration standard 160, and a second calibration standard 170. In some embodiments, the disclosed components may be in liquid communication and/or data communication with each other.

In some embodiments, reactor 110 is a microreactor configured to selectively receive a water sample from a water stream and oxidize organic contaminants in the water sample to organic acids. In some embodiments, reactor 110 is configured to avoid reducing organic contaminants to $CO_2$. In some embodiments, detector 120 is in fluid communication with reactor 110 and configured to receive a water sample the reactor 110. The detector 120 may then detect organic acids within the sample and/or classify or differentiate the organic acids by carbon chain length. In some embodiments, once the detector 120 has detected and/or classified the organic acids in the water sample, the water may be released as effluent.

In some embodiments, controller 130 is an embedded controller configured to control the operation of the system 100. In some embodiments, controller 130 may be configured to monitor reactions, control electroanalytic detection, and/or perform data processing operations. In some embodiments, controller 130 is operably connected to a first valve 140 and/or second valve 150 that may be used to direct the flow of the water stream. Depending on the desired operation, the controller may direct the first valve 140 and/or second valve 150 to direct the water stream influent to the reactor 110, or through a first calibration standard 160 or second calibration standard 170. In some embodiments, the first calibration standard 160 and/or second calibration standard 170 may consist of controlled-release solid calibration standards.

In some embodiments, a bypass direct to the electroanalytical detector and/or to a reactor temperature shutoff may be included to measure existing organic acid samples directly. This configuration may prevent over-oxidation of existing organic acid samples to $CO_2$.

It will be appreciated that the system may be packaged in a form factor of substantially any dimensions depending on the desired application. In some embodiments, the overall dimensions of system 100 are approximately 4"×4"×1.5", and the mass is estimated at about 820 g.

In some embodiments, the system may comprise a lower power automated analyzer which operates in a power range between about 1,200 mA and about 1,300 mA.

In some embodiments, a doped nickel catalytic surface or a specific, mixed metal-metal oxide catalyst in the electrocatalytic reactor provides selective oxidation of low molecular weight, polar organics to organic acids. The metal-metal oxide catalytic reactor may provide benefits including, for example, a supplemental oxygen source, selective oxidation to organic acids, limited or reduced deep oxidation to CO2, reduced susceptibility to poisoning, and/or long operational life.

An exemplary oxidation reaction of acetone to CO2 is shown below. It will be appreciated that the oxidation reaction of other organics may vary.

The first step of the exemplary reaction is rapid for most organics. The second step (organic acids to CO2) is slower, requires more power, and requires additional oxygen. The second step may also result in the requirement of TIC removal prior to TOC measurement.

The disclosed approach uses a controlled oxidation reactor to oxidize organics only to the acid, followed by detection of the acid using electroanalytical or a combination of electroanalytical and spectrophotometric or conductivity detectors. In some embodiments, the selectivity and activity of the catalyst, and the reaction kinetics may be controlled. Controlling these features and using them together provides a high degree of flexibility.

In some embodiments, the electrochemical measurement of reaction kinetics at the internal surface of an electrocatalytic reactor tube(s) or electrodes may be accomplished using an adaptation of voltammetric detection technologies. This approach provides a new capability to monitor reaction kinetics and may be used in real-time to validate whether the oxidation process is slowing or substantially complete and that deep oxidation to $CO_2$ is not occurring. The monitoring and validation of reaction kinetics in real-time allows a controller, operably connected to the reactor, to control and adjust the performance of the reactor in response to a wide variety of changing conditions. In some embodiments, the controller is used to record reactor and reaction data over time and adjust its performance based on previously gathered and analyzed data.

In some embodiments, the disclosed organic acid detection technique is based on complexation of organic acids with amine functional groups (Schiff base reaction) followed by cathodic or adsorptive stripping of the analyte complex to yield a peak whose applied potential identifies the species according to its electromotive potential. The complexation method has the potential to increase analytical sensitivity and specificity. The current required for the desorption step is directly proportional to the concentration of the analyte. Furthermore, given that different complexes desorb from the electrode at different potentials, the specific organic acid being detected (e.g. formic, acetic, propionic, etc.) can be identified and quantified individually, allowing a partial degree of speciation of the original contaminant based on carbon chain length.

In some embodiments, the analytical sensitivity of this approach may be in the range of a full-sized TOC analyzer which typically have a 50 ppb quantitation limit. Based on the electronic capability to measure low nanoamp currents using the disclosed electronics, the disclosed systems have the potential to measure ppt levels of organic acids. In some embodiments, combining the disclosed electroanalytical approach with differential conductivity and/or spectrophotometry to determine functional groups may also be performed to improve speciation capabilities.

Calibration approaches for the disclosed systems consist of long-life, controlled-release solid calibration standards. The very small liquid volumes used for the disclosed analyzer will result in a very long operational life.

EXAMPLES

During development of the disclosed systems and methods, microreactors for selective oxidation of organics to organic acids were fabricated. In an example, two types of reactors were used. Reactor number (70323-02) is based on a nickel 1/16" tube shell with proprietary dopants. Reactor number (70418-01) is based on a metal oxide reactor.

Eight reactors were previously prepared using two different techniques, chemical vapor deposition and electrolytic deposition. A ten-position parallel test stand was used to perform initial screening of the reactor performance. Based on this initial screening, two reactors were selected and tested for oxidative performance vs temperature.

The reactors were mounted in the test stand and samples were analyzed by gas chromatography and NDIR to determine conversion rates for binary mixtures of three common organic contaminants, isopropanol (IPA), ethanol, and acetic acid. These three compounds differ in their oxidative performance to such a degree that they provide a highly informative assessment of the ability of the microreactor to perform selective oxidation, i.e. oxidation to acetic acid without producing TIC. The purpose of these tests was to define the catalyst, temperature range, and kinetic environment at which the following three conditions could be met: (1) IPA, a typically recalcitrant compound in commercial TOC analyzers, is oxidized to acetone, then subsequently to acetic acid (one of two possible routes for acetone oxidation); (2) Ethanol is oxidized to Acetic acid; and (3) Acetic acid is not oxidized to TIC.

Figure 2:
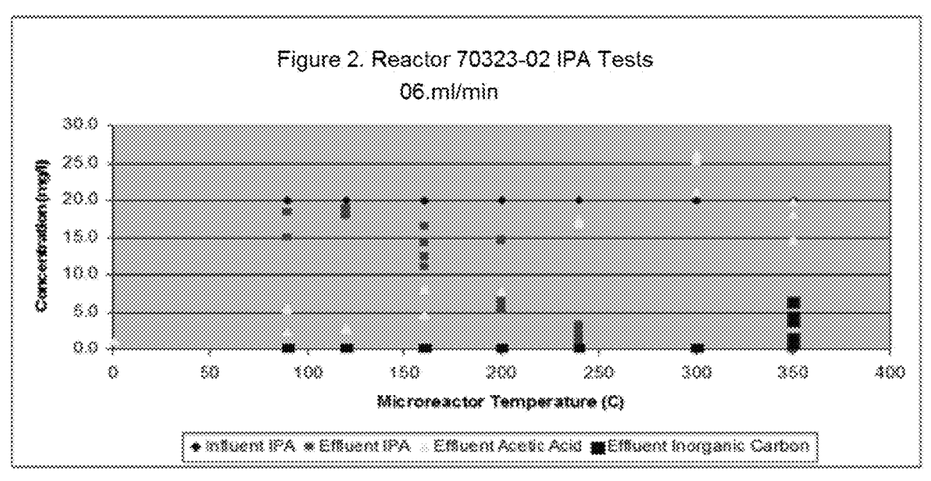
FIG. 2 is a graph showing results of a reactor according to an example embodiment.
Figure 3:
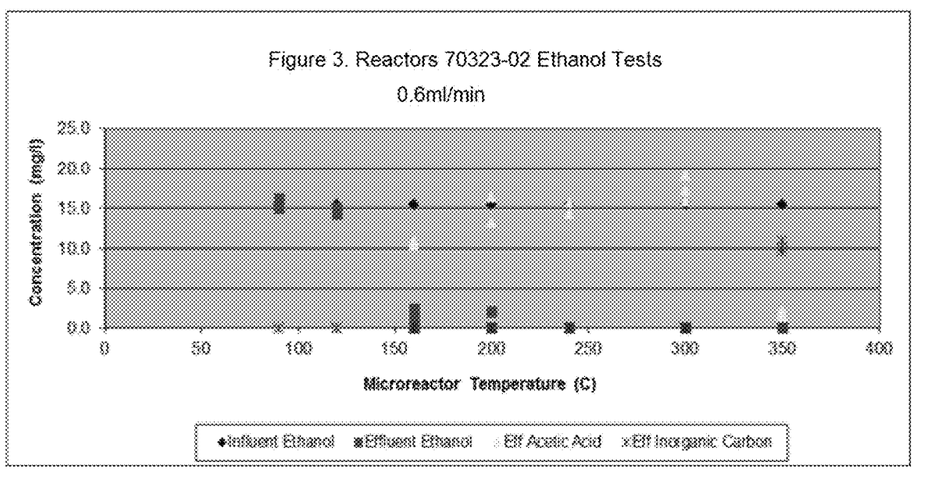
FIG. 3 is a graph showing results of a reactor according to an example embodiment.
Figure 4:
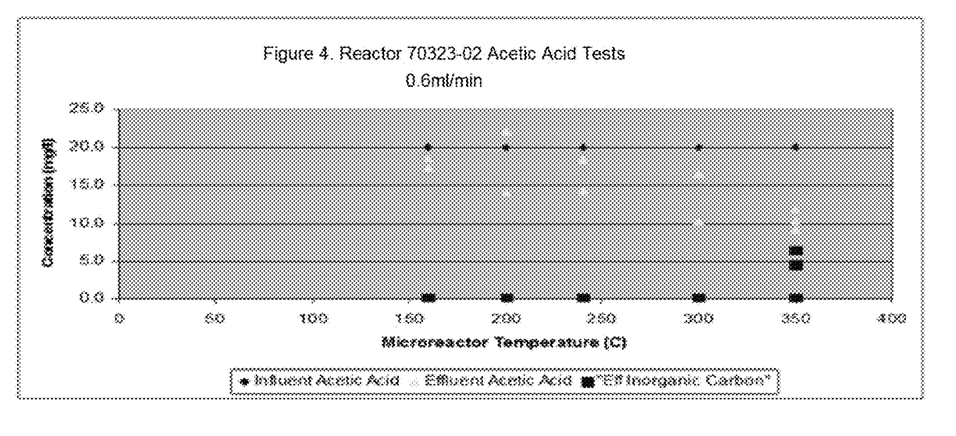
FIG. 4 is a graph showing results of a reactor according to an example embodiment.
Figure 5:
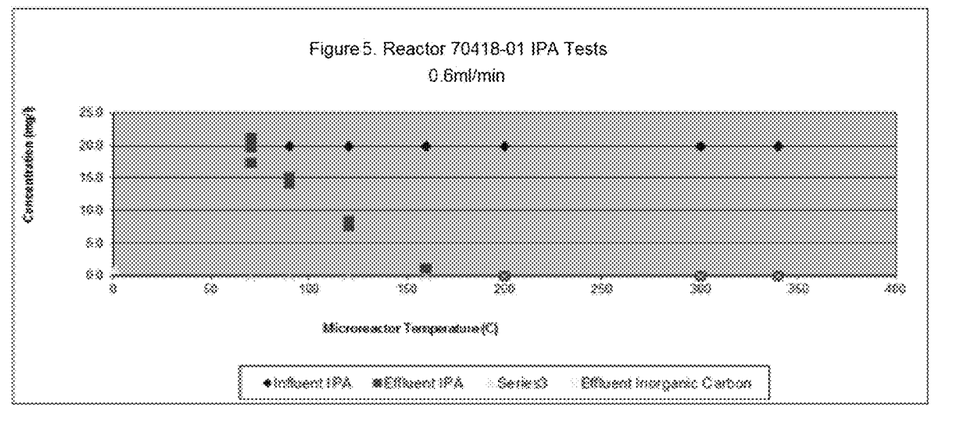
FIG. 5 is a graph showing results of a reactor according to an example embodiment.
Figure 6:
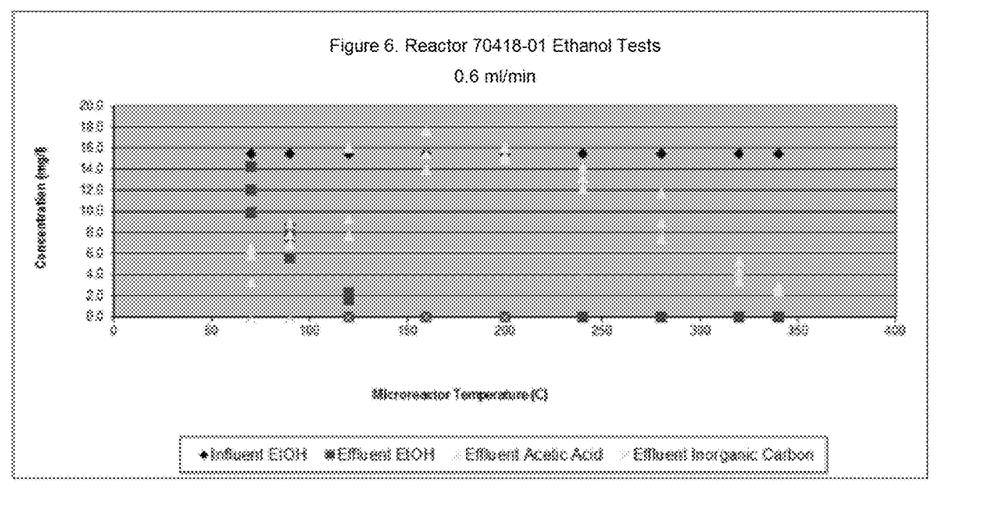
FIG. 6 is a graph showing results of a reactor according to an example embodiment.
Figure 7:
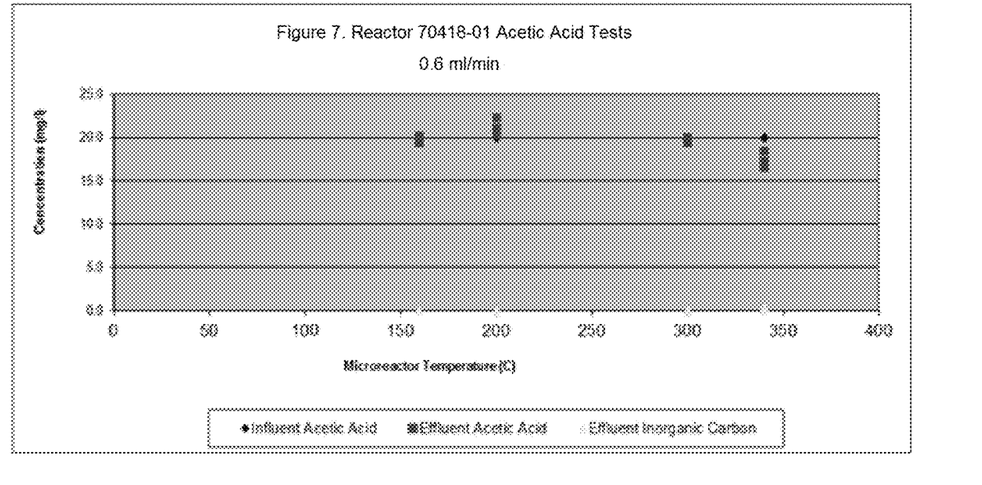
FIG. 7 is a graph showing results of a reactor according to an example embodiment.

The data for the Reactor 70323-02 are shown in FIGS. 2, 3, and 4. Data for Reactor 70418-01 are shown in FIGS. 5, 6, and 7. Over 140 samples were taken and analyzed by NDIR (TIC) and gas chromatography-FID (alcohols & acetic acid). The tests show a broad range of temperature at which the desired performance is observed. Overall, the reactor performance in the range of about 150° C. to about 250° C. range provides the preferred results. In disclosed embodiments, the reactor may be operated at temperatures as low as about 200° C., about 180° C., about 170° C., about 160° C., about 140° C., about 130° C. about 120° C. about 110° C. or about 100° C. Disclosed embodiments of the reactor may be operated at temperatures as high as about 200° C., about 220° C., about 230° C., about 240° C., about 260° C., about 270° C., about 280° C., or about 300° C. The preferred mixed metal-metal oxide reaction temperatures are somewhat lower than the doped nickel. It will be appreciated that the exact determination of reactor design will depend on many conditions including the operating conditions and the range of contaminants expected to be encountered.

During development a prototype was used to begin testing of the disclosed electroanalytical method for detection of organic acids by Schiff's base reaction with a ligand containing a single amine functional group. In some embodiments, the method is dependent upon reaction of the carboxylic acid functional group from the organic acid analyte with an amine functional group from the added ligand to form the Schiff base. Schiff bases are of the general formula R1R2C=N—R3, where R3 is a phenyl or alkyl group that makes the Schiff base a stable imine. This imine is then accumulated by either adsorption or electrochemical accumulation on the surface of an electrode. A cathodic scan is then run across the electrode, desorbing the analyte complex (the Schiff base). The reaction proceeds at standard temperature and pressure, and no catalysts are required; therefore, it can be conducted in situ within the detector. The reaction with acetic acid is shown below.

Figure 8:
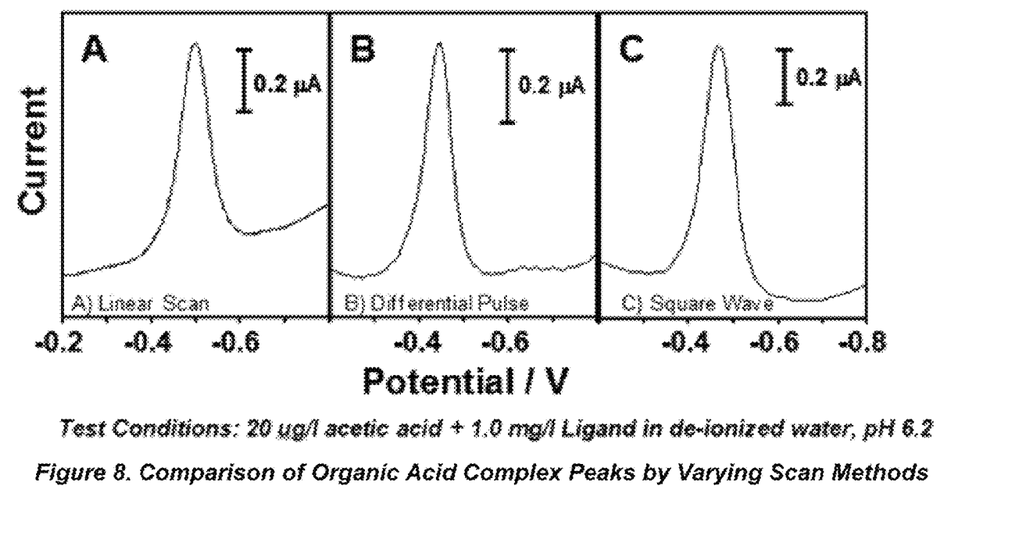
FIG. 8 illustrates a graph comparing complex peaks according to example embodiments.

Schiff Base Reaction of Acetic Acid with Proprietary Ligand $$CH_3—CH_2COOH + H_2N—R \xrightarrow{STP}$$
Organic Acid    ELS Ligane
$$CH_3—CH_2—C=N—R + H_2O$$
Schiff Base Analyte Preliminary feasibility tests were conducted at three concentrations. The tests were conducted using the prototype detector cell discussed above and a PAR Model 384B and a custom software package for data plotting. The tests show that excellent peak shape is obtained at the ppb level, and that the peaks are quantitative. The characteristics of the cathodic scan can affect the electrode response as shown in FIG. 8. In all three cases, quantifiable peaks were obtained.

In some embodiments, influent and effluent TOC, TIC and Total Carbon may be measured and/or calculated to evaluate system performance. Gas Chromatography and HPLC may be used additionally and/or alternatively to analyze for specific species of contaminants. These tests may be used to validate the mechanical and electronic subsystems to determine instrument operating range, conduct interference studies, and determine detector accuracy and precision.

Utilizing the design shown in FIG. 1, a prototype analyzer may be fabricated. The analyzer may include an embedded detector. In some embodiments, the detector may have the functionality as the prototype unit discussed. Combining the disclosed electroanalytical approach with electrochemical concentration methods and sequential detection capabilities (such as IR & spectrophotometry) can expand the instrument capabilities by providing organic contaminant speciation Some embodiments of the disclosed system and associated analytical instrumentation are configured to automatically calibrate with respect to TOC and/or TIC. The system may be configured to include multiple fluidic pathways so that portions of an aqueous water stream or water source may be directed through the disclosed reactor system and/or a calibration module. In certain embodiments, the calibration module includes a solid-phase material for removing existing levels of organic carbon and/or inorganic carbon. A known or predetermined amount of organic carbon and/or inorganic carbon may then be added to that portion of the aqueous stream to form an aqueous calibration stream. The aqueous calibration stream may be directed to the analytical instrumentation of the disclosed system, which then determines the amount of total organic carbon content of said aqueous calibration stream by oxidizing the total organic carbon to organic acids, and generating an output to said analytical instrumentation based on the predetermined amount of the total organic carbon added by said flow through solid-phase modules. The system may then calibrate its response output based on the predetermined carbon concentration of the calibration stream.

In an alternative embodiment, the analytical instrumentation of the disclosed system may be used to independently determine the type of and/or concentration of organic acid present in an existing water supply.

Figure 9:
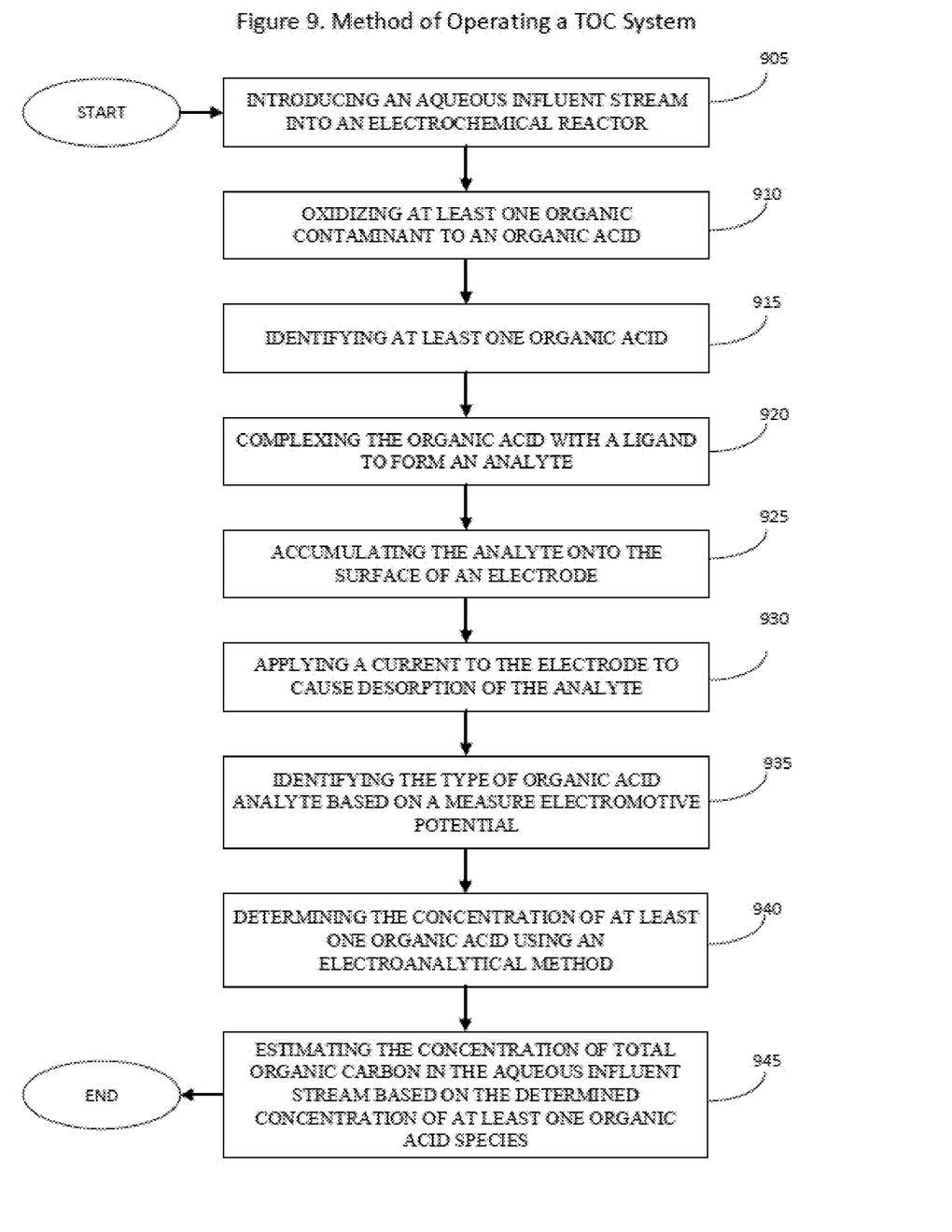
FIG. 9 is a flowchart illustrating a method of estimating the concentration of TOC according to an example embodiment.

FIG. 9 shows a flow chart of a method the operation of the disclosed system according to an example embodiment. The disclosed method commences at step 905, introducing an aqueous influent stream into an electrochemical reactor. In some embodiments, the aqueous stream comprises at least one organic contaminant. Step 910 comprises oxidizing at least one organic contaminant to an organic acid. This step may be performed using a controller operably connected to a reactor. In some embodiments, the controller is configured to substantially prevent oxidation to carbon dioxide. Step 915 comprises identifying at least one organic acid. In some embodiments, an electroanalytical method will be used. In some embodiments, the electroanalytical method for identifying the organic acid comprises, at step 920, complexing the organic acid with a ligand to form an analyte, at step 925, accumulating the analyte onto the surface of an electrode, at step 930, applying a current to the electrode to cause desorption of the analyte, and at step 935, identifying the type of organic acid analyte based on a measure electromotive potential.

Method 900 continues at step 940 comprising, determining the concentration of at least one organic acid using an electroanalytical method. In some embodiments, the electroanalytical method for determining the concentration of at least one organic acid comprises analyzing the current applied to cause desorption of the analyte. Step 945 comprises estimating the concentration of total organic carbon in the aqueous influent stream based on the determined concentration of at least one organic acid species.

In some embodiments, the disclosed methods may optionally comprise maintaining the temperature of the reactor between about 150° C. and about 250° C. In some embodiments, the reaction kinetics are monitored at the surface of an electrode to control the oxidation process. In some embodiments, the ligand comprises a single amine functional group. In some embodiments, the disclosed method optionally comprises differentiating at least one organic acid using spectrophotometry. In some embodiments, the spectrophotometry comprises IR spectrophotometry or UV-vis spectroscopy or a combination thereof.

In some embodiments, the disclosed method optionally comprises analyzing the current applied to the electrode to cause desorption of the analyte to at least partially determine chemical structure of the analyte.

In some embodiments, the aqueous influent stream comprises a substantially constant level of dissolved carbon dioxide. In some embodiments, the at least one organic acid contaminant comprises volatile organic compounds.

Some disclosed embodiments relate to a process for automatically calibrating analytical instrumentation with respect to total organic carbon. In some embodiments, the process comprises providing flow-through solid-phase modules for calibration of the analytical instrumentation. The process also comprises introducing an aqueous influent stream into said flow-through solid phase modules for removing existing levels of organic carbon and adding to the aqueous influent stream a predetermined amount of total organic carbon to form an aqueous calibration stream. In some embodiments, the process comprises introducing the aqueous calibration stream to said analytical instrumentation and analyzing the total organic carbon content of said aqueous calibration stream by oxidizing the total organic carbon to organic acids and generating an out-put to said analytical instrumentation based on the predetermined amount of the total organic carbon added by said flow through solid-phase modules, thereby calibrating the analytical instrumentation.

Some embodiments relate to a system for treating a water supply. In some embodiments, the system comprises an aqueous influent stream; a reactor in fluid communication with the influent stream; a detector in fluid communication with the influent stream, wherein the detector is configured to detect organic acids using accumulation and desorption performed at an electrode surface; and a controller operably connected to the reactor and detector, wherein the controller is configured to control the reactor and monitor reaction kinetics; and wherein controller directs the reactor to at least partially oxidize organic carbon. Some embodiments further comprise a spectrophotometer. In some embodiments, the spectrophotometer is selected from the group consisting of infrared spectrophotometers and UV-vis spectroscopes. Some embodiments further comprise a ligand, wherein the ligand comprises an amine functional group. In some embodiments, the controller is configured to adjust the operation of the reactor in response to changing reaction kinetics. In some embodiments, the controller is configured to control the reactor in response to data from the detector. In some embodiments, the system is substantially free of toxic materials. In some embodiments, the controller is configured to be remotely controllable. In some embodiments, the reactor is a microreactor. In some embodiments, the reactor, detector, and controller are housed in one self-contained module.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

In this description, numerous specific details have been set forth. It is to be understood, however, that implementations of the disclosed technology may be practiced without these specific details. In other instances, well-known methods, structures and techniques have not been shown in detail in order not to obscure an understanding of this description. References to "some examples," "other examples," "one example," "an example," "various examples," "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrases "in one example," "in one embodiment," or "in one implementation" does not necessarily refer to the same example, embodiment, or implementation, although it may.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed:

1. A method of treating a water supply, the method comprising:
    introducing an aqueous influent stream into an electrochemical reactor, wherein the aqueous stream comprises at least one organic contaminant;
    oxidizing at least one organic contaminant to an organic acid using a controller operably connected to the reactor, wherein the controller is configured substantially prevent oxidation to carbon dioxide;
    identifying at least one organic acid using an electroanalytical method, wherein the electroanalytical method for identifying the organic acid comprises complexing the organic acid with a ligand to form an analyte, accumulating the analyte onto the surface of an electrode, applying a current to the electrode to cause desorption of the analyte, and identifying the type of organic acid analyte based on a measure electromotive potential;
    determining the concentration of at least one organic acid using an electroanalytical method, wherein the electroanalytical method for determining the concentration of at least one organic acid comprises analyzing the current applied to cause desorption of the analyte;
    estimating the concentration of total organic carbon in the aqueous influent stream based on the determined concentration of at least one organic acid species.

2. The method of claim 1, further comprising maintaining the temperature of the reactor between about 150° C. and about 250° C.

3. The method of claim 1, wherein reaction kinetics are monitored at the surface of an electrode by voltammetric detection.

4. The method of claim 1 wherein the ligand comprises a single amine functional group.

5. The method of claim 1, further comprising differentiating at least one organic acid using spectrophotometry.

6. The method of claim 5, wherein the spectrophotometry comprises IR spectrophotometry or UV-vis spectroscopy or a combination thereof.

7. The method of claim 1, further comprising analyzing the current applied to the electrode to cause desorption of the analyte to at least partially determine chemical structure of the analyte.

8. The method of claim 1, wherein the aqueous influent stream comprises a substantially constant level of dissolved carbon dioxide.

9. The method of claim 1, wherein the at least one organic acid contaminant comprises volatile organic compounds.

* * * * *